United States Patent
Kraemer et al.

(10) Patent No.: US 11,208,670 B2
(45) Date of Patent: Dec. 28, 2021

(54) METHOD FOR PRODUCING A FERMENTATION PRODUCT

(71) Applicant: BASF ENZYMES LLC, San Diego, CA (US)

(72) Inventors: Marco Kraemer, Cologne (DE); Vitaly Svetlichny, Cologne (DE); Eva Eilert, Cologne (DE)

(73) Assignee: BASF Enzymes LLC, San Diego, CA (US)

( * ) Notice: Subject to any disclaimer, the term of this patent is extended or adjusted under 35 U.S.C. 154(b) by 11 days.

(21) Appl. No.: 15/770,079

(22) PCT Filed: Sep. 6, 2016

(86) PCT No.: PCT/EP2016/070957
§ 371 (c)(1),
(2) Date: Apr. 20, 2018

(87) PCT Pub. No.: WO2017/067698
PCT Pub. Date: Apr. 27, 2017

(65) Prior Publication Data
US 2018/0312879 A1  Nov. 1, 2018

Related U.S. Application Data

(60) Provisional application No. 62/245,054, filed on Oct. 22, 2015.

(30) Foreign Application Priority Data

Oct. 22, 2015  (EP) .................................... 15191039

(51) Int. Cl.
*C12P 7/06* (2006.01)
*C12P 19/14* (2006.01)
*C12P 7/40* (2006.01)
*C12P 19/02* (2006.01)
*C12P 7/14* (2006.01)

(52) U.S. Cl.
CPC ................. *C12P 7/06* (2013.01); *C12P 7/065* (2013.01); *C12P 7/14* (2013.01); *C12P 7/40* (2013.01); *C12P 19/02* (2013.01); *C12P 19/14* (2013.01); *C12Y 302/01004* (2013.01); *C12Y 302/01006* (2013.01); *C12Y 302/01015* (2013.01); *C12Y 304/00* (2013.01); *Y02E 50/10* (2013.01)

(58) Field of Classification Search
CPC combination set(s) only.
See application file for complete search history.

(56) References Cited

U.S. PATENT DOCUMENTS

| 5,306,633 A | 4/1994 | Gottschalk et al. |
| 8,962,286 B2 * | 2/2015 | Milos ........................ C12F 3/10 435/136 |

FOREIGN PATENT DOCUMENTS

| WO | 2006/078256 A2 | 7/2006 | |
| WO | 2009/079210 A2 | 6/2009 | |
| WO | 2011/150313 A1 | 12/2011 | |
| WO | 2012/049170 A2 | 4/2012 | |
| WO | 2012/084225 A1 | 6/2012 | |
| WO | WO-2012084225 A1 * | 6/2012 | ........... C12N 9/2482 |
| WO | 2014/127851 A1 | 8/2014 | |
| WO | 2016/020101 A1 | 2/2016 | |
| WO | 2016/020103 A1 | 2/2016 | |
| WO | 2016/020468 A1 | 2/2016 | |

OTHER PUBLICATIONS

EP16766876.3 Office Action dated Oct. 8, 2019.
Ondas et al. "Conversion of Corn Fiber into Fuel Ethanol," Nova Biotechnologica, 2009, 9(2):183-190.
"Viscozyme L Product Sheet," Novozymes A/S, May 2002, 1-2.
PCT/EP2016/070957 International Search Report dated Nov. 14, 2016.
Li et al. "Monosaccharides and Ethanol Production from Superfine Ground Sugarcane Bagasse Using Enzyme Cocktail," BioResources, Mar. 21, 2014, North Carolina State University, College of Natural Resources, US, vol. 9, No. 2, pp. 2529-2540.
Li et al. "Synergism of cellulase, xylanase, and pectinase on hydrolyzing sugarcane bagasse resulting from different pretreatment technologies," Bioresource Technology, Mar. 2014, vol. 155, pp. 258-265, Elsevier BV, GB.
Scheller et al. "Hemicelluloses," Annu Rev Plant Biol., 2010, 61:263-289.
Reen et al. Nucleotide Sequence, SwissProt Accession No. Q8X212.
Dietrich et al. Nucleotide Sequence (Large Scale Genomic DNA), SwissProt Accession No. Q750W4.
Margolles-Clark et al. Nucleotide Sequence, UniProt KB Accession No. Q92458.

* cited by examiner

*Primary Examiner* — Heidi Reese
(74) *Attorney, Agent, or Firm* — DLA Piper LLP (US)

(57) ABSTRACT

The present technology relates to improved processes of producing fermentation products from starch-containing material using fermenting microorganisms comprising a pentose (i.e., C5 sugar) fermenting yeast cell, suitable for fermentation of a sugar composition comprising C5 sugar(s) in combination with an enzyme composition.

9 Claims, 1 Drawing Sheet

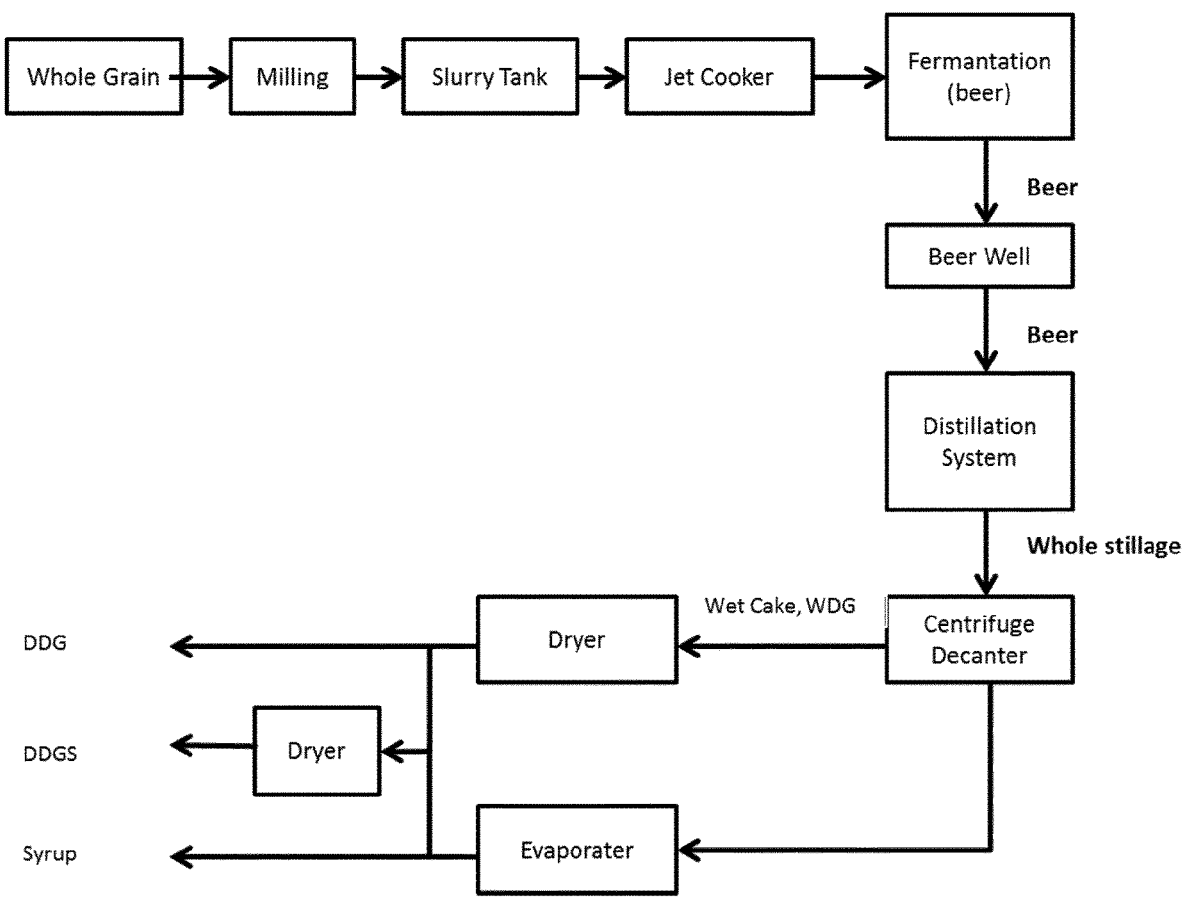

METHOD FOR PRODUCING A FERMENTATION PRODUCT

CROSS REFERENCE TO RELATED APPLICATIONS

This application is a US national phase application under 35 USC § 371 of International patent application no. PCT/EP2016/070957, filed Sep. 6, 2016, which itself claims priority to European application no. 15191039.5, filed Oct. 22, 2015, and U.S. provisional application No. 62/245,054, filed Oct. 22, 2015. Each of the applications referred to in this paragraph are herein incorporated by reference in their entireties.

FIELD OF THE INVENTION

The present disclosure relates to improved processes of producing fermentation products from starch-containing material using fermenting microorganisms comprising a pentose (i.e., C5 sugar) fermenting yeast cell, suitable for fermentation of a sugar composition comprising C5 sugar(s) in combination with an enzyme composition.

BACKGROUND OF THE INVENTION

A vast number of commercial products that are difficult to produce synthetically are today produced by fermenting organisms. Such products include alcohols (e.g., butanol, ethanol, methanol, 1,3-propanediol), organic acids (e.g., acetic acid, citric acid, gluconate, gluconic acid, itaconic acid, lactic acid, succinic acid, 2,5-diketo-D-gluconic acid), ketones (e.g., acetone); amino acids (e.g., glutamic acid), gases (e.g., $H_2$ and $CO_2$), and more complex compounds, including, for example, antibiotics (e.g., penicillin and tetracycline), enzymes; vitamins (e.g., riboflavin, $B_{12}$, beta-carotene), and hormones. Fermentation is also commonly used in the consumable alcohol (e.g., beer and wine), dairy (e.g., in the production of yogurt and cheese), leather, and tobacco industries.

Fermentation products, such as ethanol, are produced by first degrading starch-containing material into fermentable sugars by liquefaction and saccharification and then converting the sugars directly or indirectly into the desired fermentation product using a fermenting organism. Liquid fermentation products such as ethanol are recovered from the beer mash (often referred to as "fermented mash" or "beer"), e.g., by distillation, which separates the desired fermentation product from other liquids and/or solids. The remaining fraction, referred to as "whole stillage", is dewatered and separated into a solid and a liquid phase, e.g., by centrifugation. The solid phase is referred to as "wet cake" (or "wet grains" or "WDG") and the liquid phase (supernatant) is referred to as "thin stillage". Dewatered wet cake is dried to provide "Distillers Dried Grains" (DDG) used as nutrient in animal feed. Thin stillage is typically evaporated to provide condensate and syrup (or "thick stillage") or may alternatively be recycled directly to the slurry tank as "backset". Condensate may either be forwarded to a methanator before being discharged or may be recycled to the slurry tank. The syrup consisting mainly of limit dextrins and non-fermentable sugars may be blended into DDG or added to the wet cake before drying to produce "Distillers Dried Grains with Solubles" (DDGS).

Ethanol plants have struggled to maintain profitability, which is highly variable depending upon corn price, demand and price of DDGS, tax credits, gasoline consumption, ethanol exports, and changes to the Renewable Fuels Standard (RFS) mandates. New technologies for energy savings, higher yield of ethanol and higher value for co-products as well as various oil separation technologies contribute to the profitability of producing ethanol.

Therefore, there is a need for providing processes that can increase the yield of the fermentation product and thereby reduce the production costs. It is an object of the present invention to provide improved processes for producing fermentation products.

SUMMARY OF THE INVENTION

The present disclosure relates to processes of producing fermentation products from starch-containing material using a pentose fermenting yeast cell in combination with an enzyme composition.

In one aspect, the present disclosure relates to methods of producing a fermentation product from starch-containing material, said method comprising the steps of:
i) Converting starch-containing material to fermentable sugars,
ii) Fermentation of the fermentable sugars with fermenting microorganisms to beer mash,
iii) Subjecting the fermentation medium before and/or during the fermentation process to an enzyme composition comprising a hemicellulase like a xylanase or a mannanase and at least a further enzyme selected from the group consisting of pectinase, cellulase, glucanase and protease,
iv) Separation of the fermentation product in the beer mash,
wherein the fermenting microorganisms comprise pentose fermenting yeast cells and/or pentose and glucose fermenting yeast cells.

In another aspect, the present disclosure relates to method of producing a fermentation product, comprising
(a) Liquefying a starch-containing material with an alpha-amylase; optionally pre-saccharifying the liquefied material before step (b),
(b) saccharifying the liquefied material,
(c) Fermenting using fermenting microorganisms; wherein an enzyme composition comprising a hemicellulase like a xylanase or a mannanase and at least a further enzyme selected from the group consisting of pectinase, cellulase, glucanase and protease are present or added during the optional pre-saccharification step, saccharification step (b), and/or in particular during and/or after the fermentation step (c), or simultaneous saccharification and fermentation, and wherein the fermenting microorganisms comprise pentose fermenting yeast cells and/or pentose and glucose fermenting yeast cells.

The present disclosure further relates to a process for producing ethanol from the fermentation of pentose and hexose, comprising the step of: culturing pentose fermenting yeast cells in a pentose- and hexose containing sugar composition in combination together with hexose fermenting yeast cells and in combination with an enzyme composition comprising a hemicellulase like a xylanase or a mannanase and at least a further enzyme selected from the group consisting of pectinase, cellulase, glucanase and protease under suitable fermentation conditions for a period of time sufficient to allow the fermentation of pentose and hexose to ethanol.

BRIEF DESCRIPTION OF THE DRAWING

FIG. 1 schematically shows an ethanol production process.

DETAILED DESCRIPTION OF THE INVENTION

The object of the present disclosure is to provide methods/processes of producing fermentation products from starch- and hemicellulose containing material using a pentose-fermenting organism to improve the ethanol yield in $1^{st}$ generation ethanol fermentation processes.

The present disclosure further relates to a process for producing ethanol in a $1^{st}$ and/or $2^{nd}$ generation ethanol production process from the fermentation of pentose and hexose, comprising the step of culturing pentose fermenting yeast cells in a pentose- and hexose containing sugar composition in combination with hexose fermenting yeast cells and in combination with an enzyme composition comprising a hemicellulase (e.g. xylanase or mannanase) and at least a further enzyme selected from the group consisting of pectinase, cellulase, glucanase and protease under suitable fermentation conditions for a period of time sufficient to allow the fermentation of pentose and hexose to ethanol.

In an advantageous embodiment, the present disclosure pertains to methods of producing a fermentation product from starch/hemicellulose-containing material, said method comprising the steps of:
i) Converting starch/hemicellulose-containing material to fermentable sugars,
ii) Fermentation of the fermentable sugars with fermenting microorganisms to beer mash,
iii) Subjecting the fermentation medium before and/or during the fermentation process to an enzyme composition comprising a hemicellulase like xylanase or mannanase and at least a further enzyme selected from the group consisting of pectinase, cellulase, glucanase and protease,
iv) Separation of the fermentation product in the beer mash,
wherein the fermenting microorganisms comprise pentose fermenting yeast cells and/or pentose and glucose fermenting yeast cells.

By subjecting the fermentation medium during the fermentation process to an enzyme composition according to the present disclosure in combination with pentose fermenting yeast cells (C5 yeast cells) and hexose fermenting microorganism(s), a decrease fermenting time could be expected as well as an increase in ethanol production.

Production of a fermentation product is typically divided into the following main process stages:
a) Reducing the particle size of starch-containing material, e.g., by dry or wet milling,
b) Cooking the starch-containing material in aqueous slurry to gelatinize the starch,
c) Liquefying the gelatinized starch-containing material in order to break down the starch (by hydrolysis) into maltodextrins (dextrins),
d) Saccharifying the maltodextrins (dextrins) to produce low molecular sugars (e.g., DP1-2) that can be metabolized by a fermenting organism,
e) Fermenting the saccharified material using a suitable fermenting organism directly or indirectly converting low molecular sugars into the desired fermentation product,
f) Recovering the fermentation product, e.g., by distillation in order to separate the fermentation product from the beer mash.

Subjecting the fermentation medium before and/or during the fermentation process to an enzyme composition according to the present disclosure results in a high amount of C5-sugars like xylose or arabinose from the hemicellulose comprised in the starch-containing material as a starting material for the C5-yeasts. Therefore, with the conversion of the C5-sugars by the C5-yeasts, the overall ethanol amount from the fermentation process increases.

The beer mash contemplated according to the present disclosure may be the product resulting from a fermentation product production process including above-mentioned steps a) to f). However, the beer mash may also be the product resulting from other fermentation product production processes based on starch- and/or lignocellulose-containing starting material.

In an advantageous embodiment, the present disclosure pertains to methods of producing a fermentation product, comprising
(a) Liquefying a starch-containing material with an alpha-amylase; optionally pre-saccharifying the liquefied material before step (b),
(b) Saccharifying the liquefied material,
(c) Fermenting using fermenting microorganisms; wherein an enzyme composition comprising a hemicellulase like xylanase or mannanase and at least a further enzyme selected from the group consisting of pectinase, cellulase, glucanase and protease are present or added during the optional pre-saccharification step, saccharification step (b), and/or in particular during the fermentation step (c), or simultaneous saccharification and fermentation, and wherein the fermenting microorganisms comprise pentose fermenting yeast cells and/or pentose and glucose fermenting yeast cells.

Characterization of the Fermenting Microorganism

The fermenting microorganism may be a fungal organism, such as yeast, or bacteria. Suitable bacteria may, e.g., be *Zymomonas* species, such as *Zymomonas mobilis* and *Escherichia coli*.

Examples of filamentous fungi include strains of *Penicillium* species. Preferred organisms for ethanol production are yeasts, e.g., *Pichia* or *Saccharomyces*. Preferred yeasts according to the disclosure are *Saccharomyces* species, in particular *Saccharomyces cerevisiae* or baker's yeast.

The pentose fermenting yeast cells typically contain genes of a pentose metabolic pathway non-native to the yeast and/or that allow the yeast cell to convert pentose(s). An example of a pentose-fermenting microorganism is described in the WO 2011/150313.

In one embodiment, the yeast cell may comprise one or two or more copies of one or more xylose isomerases and/or one or two or more copies of one or more xylose reductase and xylitol dehydrogenase genes, allowing the yeast cell to convert xylose. In an embodiment thereof, these genes may be integrated into the yeast cell genome. In another embodiment, the yeast cell comprises the genes araA, araB and araD. It is then able to ferment arabinose. In one embodiment of the invention the yeast cell comprises xylA-gene, XYL1 gene and XYL2 gene and/or X S7-gene, to allow the yeast cell to ferment xylose; deletion of the aldose reductase (GRE3) gene; overexpression of PPP-genes TALL TKL1, RPE1 and RKI1 to allow the increase of the flux through the pentose phosphate pass-way in the cell, and/or overexpression of GAL2 and/or deletion of GAL80. Despite of the presence of the above genes, suitable pentose or other metabolic pathway(s) may be introduced in the yeast cells that were non-native (wild type).

In an embodiment, the pentose fermenting yeast cell is derived from industrial yeast by disruption of hexokinase. An industrial cell and industrial yeast cell may be defined as follows. The living environments of (yeast) cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. In one embodiment, the industrial yeast cell is constructed on the basis of an industrial host cell, wherein the construction is conducted as described hereinafter. Examples of industrial yeast (*Saccharomyces cerevisiae*) are Ethanol Red® (Fermentis), Fermiol® (DSM Food Specialties B.V.) and Thermosacc® (Lallemand Biofuels and Distilled Spirits).

In some advantageous embodiments the fermenting organism may ferment both hexoses and pentoses. An example for such a yeast cell is disclosed in WO2012/049170 A2.

As mentioned above, the fermenting organism is preferably yeast, e.g., a strain of *Saccharomyces cerevisiae* or *Saccharomyces diastaticus*. In an advantageous embodiment a yeast strain of *Saccharomyces diastaticus* is used (SIHA Amyloferm®, E. Begerow GmbH & Co.) since their exo-amylase activity can split liquid starch and also dextrin, maltose and melibiose.

Feedstock Preparation

The feedstock for producing the fermentation product may be any starch/hemicellulose-containing material, preferably starch-containing plant material, including tubers, roots, whole grain or any combination thereof. The starch/hemicellulose-containing material may be obtained from cereals. Suitable starch/hemicellulose-containing material includes corn (maize), wheat, barley, cassava, sorghum, rye, potato, or any combination thereof. Corn is the preferred feedstock, especially when the fermentation product is ethanol. The starch-containing material may also consist of or comprise, e.g., a side stream from starch processing, e.g., C6 carbohydrate containing process streams that may not be suited for production of syrups. In particular, the starch-containing material comprises hemicelluloses like lignocellulose. A hemicellulose (also known as polyose) is any of several heteropolymers (matrix polysaccharides), such as arabinoxylans, present along with cellulose in almost all plant cell walls (see Scheller H V, Ulvskov P., Hemicelluloses. //Annu Rev Plant Biol. 2010; 61:263-89. doi: 10.1146/annurev-arplant-042809-112315). Hemicelluloses include xylan, glucuronoxylan, arabinoxylan, glucomannan, and xyloglucan. These polysaccharides contain many different sugar monomers. In contrast, cellulose contains only anhydrous glucose. For instance, besides glucose, sugar monomers in hemicellulose can include xylose, mannose, galactose, rhamnose, and arabinose. Hemicelluloses contain most of the D-pentose sugars, and occasionally small amounts of L-sugars as well. Xylose is in most cases the sugar monomer present in the largest amount, although in softwoods mannose can be the most abundant sugar.

Processes for producing fermentation products, such as ethanol, from a starch- or hemicellulose like lignocelluloses-containing material are well known in the art. In a preferred embodiment, the starch/lignocellulose containing material is milled cereals, preferably barley or corn, and the methods comprise a step of milling the cereals before step (a). The preparation of the starch/hemicellulose-containing material such as corn for utilization in such fermentation processes typically begins with grinding the corn in a dry-grind or wet-milling process. Grinding is also understood as milling, as is any process suitable for opening the individual grains and exposing the endosperm for further processing. Wet-milling processes involve fractionating the corn into different components where only the starch fraction enters into the fermentation process. Dry-grind processes involve grinding the whole corn kernels into meal, e.g., by hammer or roller mills, and subsequently mixing the meal with water and enzymes.

Generally two different kinds of dry-grind processes are used. The most commonly used process, often referred to as a "conventional process," includes grinding the starch/hemicellulose-containing material and then liquefying gelatinized starch at a high temperature using typically a bacterial alpha-amylase, followed by "simultaneous saccharification and fermentation" (SSF) carried out in the presence of a glucoamylase and a fermentation organism. Another well-known process, often referred to as a "raw starch hydrolysis" (RSH) process, includes grinding the starch-containing material and then simultaneously saccharifying and fermenting granular starch below the initial gelatinization temperature typically in the presence of an acid fungal alpha-amylase and a glucoamylase.

The term "alpha-amylase" means an alpha-1,4-glucan-4-glucanohydrolase (E.C. 3.2.1.1) that catalyzes the hydrolysis of starch and other linear and branched 1,4-glucosidic oligo- and polysaccharides.

Preparation of Slurry

The mash may be provided by forming a slurry comprising the milled starch/hemicellulose-containing material and brewing water. The brewing water may be heated to a suitable temperature prior to being combined with the milled starch-containing material in order to achieve a mash temperature of 45-70° C., preferably of 53-66° C., more preferably of 55-60° C. The mash is typically formed in a tank known as the slurry tank.

The aqueous slurry may contain from 10-55 wt-% dry solids, preferably 25-45 wt-% dry solids, more preferably 30-40 wt-% dry solids of the starch-containing material. The slurry is heated to above the gelatinization temperature and an alpha-amylase, preferably a bacterial and/or acid fungal alpha-amylase, may be added to initiate liquefaction (thinning). The slurry may be jet-cooked to further gelatinize the slurry before being subjected to an alpha-amylase in step (a).

Liquefaction Step

In the liquefaction step the gelatinized starch (downstream mash) is broken down (hydrolyzed) into maltodextrins (dextrins). To achieve starch hydrolysis a suitable enzyme, preferably an alpha-amylase, is added. Liquefaction may be carried out as a three-step hot slurry process. The slurry is heated to between 60-95° C., preferably 80-85° C., and an alpha-amylase may be added to initiate liquefaction (thinning). Then the slurry may be jet-cooked at a temperature between 95-140° C., preferably 105-125° C., for about 1-15 minutes, preferably for about 3-10 minutes, especially around about 5 minutes. The slurry is cooled to 60-95° C. and more alpha-amylase may be added to complete the hydrolysis (secondary liquefaction). The liquefaction process is usually carried out at a pH of 4.0 to 6.5, in particular at a pH of 4.5 to 6.

Saccharification Step

The saccharification step and the fermentation step may be performed as separate process steps or as a simultaneous saccharification and fermentation (SSF) step. The saccharification is carried out in the presence of a saccharifying enzyme, e.g., a glucoamylase, a beta-amylase or maltogenic amylase. Optionally a phytase and/or a protease is added.

Saccharification may be carried out using conditions well known in the art with a saccharifying enzyme, e.g., beta-amylase, glucoamylase or maltogenic amylase, and optionally a debranching enzyme, such as an isoamylase or a pullulanase. For instance, a full saccharification process may last up to from about 24 to about 72 hours, however, it is common to do a pre-saccharification for typically 40-90 minutes at a temperature between 30-65° C., typically about 60° C., followed by complete saccharification during fermentation in a simultaneous saccharification and fermentation (SSF) process. Saccharification is typically carried out at a temperature from 20-75° C., preferably from 40-70° C., typically around 60° C., and at a pH between 4 and 5, normally at about pH 4.5.

The most widely used process to produce a fermentation product, especially ethanol is the simultaneous saccharification and fermentation (SSF) process, in which there is no holding stage for the saccharification, meaning that a fermenting organism, such as a yeast, and enzyme(s), including the hemicellulase(s) and/or specific endoglucanase(s), may be added together. SSF is typically carried out at a temperature from 25-40° C., such as from 28-35° C., from 30-34° C., preferably around about 32° C.

Fermentation Step

The phrase "fermentation media" or "fermentation medium" refers to the environment in which fermentation is carried out and comprises the fermentation substrate, that is, the carbohydrate source that is metabolized by the fermenting organism(s). The fermentation medium may comprise other nutrients and growth stimulator(s) for the fermenting organism(s). Nutrient and growth stimulators are widely used in the art of fermentation and include nitrogen sources, such as ammonia; vitamins and minerals, or combinations thereof.

In an embodiment, fermentation is ongoing for 6 to 120 hours, in particular 24 to 96 hours.

Product Recovery

According to the invention the fermentation product may be any fermentation product, including alcohols (e.g., ethanol, methanol, butanol, 1,3-propanediol); organic acids (e.g., citric acid, acetic acid, itaconic acid, lactic acid, gluconic acid, gluconate, succinic acid, 2,5-diketo-D-gluconic acid), ketones (e.g., acetone), amino acids (e.g., glutamic acid), gases (e.g., $H_2$ and $CO_2$), and more complex compounds, including, for example, antibiotics (e.g., penicillin and tetracycline), enzymes; vitamins (e.g., riboflavin, $B_{12}$, beta-carotene), and hormones. Fermentation is also commonly used in the consumable alcohol (e.g., beer and wine), dairy (e.g., in the production of yogurt and cheese), leather, and tobacco industries. In a preferred embodiment the fermentation product is a liquid, preferably an alcohol, especially ethanol.

Whole stillage typically contains about 10-15 wt-% dry solids. Whole stillage components include fiber, hull, germ, oil and protein components from the starch-containing feedstock as well as non-fermented starch.

The whole stillage is separated into solid and liquid fractions (i.e., wet cake and thin stillage containing about 35 wt-% and 7 wt-% solids, respectively). The thin stillage is often condensed by evaporation into syrup, subsequently recombined with the wet cake and further dried into DDGS for use in animal feed.

Subsequent to fermentation the fermentation product may be separated from the fermentation medium. The beer mash may be distilled to extract the desired fermentation product or the desired fermentation product from the beer mash by micro or membrane filtration techniques. Alternatively the fermentation product may be recovered by stripping.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation as mentioned above. Ethanol with a purity of up to about 96 vol. % can be obtained, which can be used as, for example, fuel ethanol, drinking ethanol, i.e., potable neutral spirits, or industrial ethanol.

Application of Enzyme Composition

The saccharification and fermentation steps may be carried out either sequentially or simultaneously. The enzyme composition may be added during saccharification and/or after fermentation when the process is carried out as a sequential saccharification and fermentation process and before or during fermentation when steps (b) and (c) are carried out simultaneously (SSF process).

In one embodiment of the present disclosure enzymes were added during the fermentation in the production process to the fermentation medium.

In some advantageous embodiments, an enzyme composition is present or added during the optional pre-saccharification step, saccharification step (b), and/or fermentation step (c), or simultaneous saccharification and fermentation. In further examples, the fermentation medium is subjected before, during and/or after the fermentation process to an enzyme composition.

Further, by adding the enzymes according to the present disclosure to the fermentation medium or the beer mash before the distillation step is an advantage since the enzymes in the enzyme compositions are inactivated during the distillation.

The enzymes according to the present disclosure were capable of degrading components (e.g., non-starch polysaccharides) in the beer mash and/or the fermentation medium.

Details on Enzyme Composition

In an embodiment, enzyme composition comprises a hemicellulase.

In a further embodiment, enzyme composition comprises a cellulase.

In a further embodiment, enzyme composition comprises a pectinase.

In a further embodiment, enzyme composition comprises a glucanase.

In a further embodiment, enzyme composition comprises a protease.

In an embodiment, the enzyme composition comprises a hemicellulase and a pectinase.

In a further embodiment, the enzyme composition comprises a hemicellulase and a cellulase.

In a further embodiment, the enzyme composition comprises a cellulase and a glucanase.

In another embodiment, the enzyme composition comprises a glucanase and a hemicellulase.

In an advantageous embodiment, the enzyme composition comprises a hemicellulase, and a glucanase and a cellulase.

In an advantageous embodiment, the enzyme composition comprises a hemicellulase, and a glucanase and a pectinase.

Hemicellulases

Hemicellulases as used herein are enzymes capable to break down hemicellulose like lignocellulose. Any hemicellulase suitable for use in hydrolyzing hemicellulose, preferably into xylose, may be used. Preferred hemicellulases include acetylxylan esterases, endo-arabinases, exo-arabinases, arabinofuranosidases, feruloyl esterase, endo-galactanases, exo-galactanases, glucuronidases, mannanases, xylanases, and mixtures of two or more thereof. Preferably, the hemicellulase for use in the present invention is an exo- and endo-acting hemicellulase, and more preferably, the hemicellulase is an exo-acting hemicellulase which has the ability to hydrolyze hemicellulose under acidic conditions of below pH 7, preferably pH 3-7.

In one aspect, the hemicellulase(s) comprises a commercial hemicellulolytic enzyme preparation. Examples of commercial hemicellulolytic enzyme preparations suitable for use in the present invention include, for example, Cellic® HTec, Cellic® HTec2, Viscozyme®, Ultraflo® and Pulpzyme® HC (from Novozymes A/S), Accellerase® XY, Accellerase® XC (from Genencor Int.), Ecopulp® TX-200A (from AB Enzymes GmbH), Bakezyme® HSP 6000 (from DSM Food Specialties), Depol™ 333P, Depol™ 740L, and Depol™762P (from Biocatalysts Ltd).

In an embodiment of the present disclosure the xylanase may preferably be of microbial origin, such as of fungal origin (e.g., *Aspergillus, Fusarium, Humicola, Meripilus*, and *Trichoderma*) or from a bacterium (e.g., *Bacillus*). In a preferred embodiment the xylanase is derived from a filamentous fungus, preferably derived from a strain of *Aspergillus*, such as *Aspergillus aculeatus*; or a strain of *Humicola*, preferably *Humicola lanuginosa*. Examples of xylanases useful in the methods of the present invention include, but are not limited to *Aspergillus aculeatus* xylanase (GeneSeqP:AAR63790; WO 94/21785), *Aspergillus fumigatus* xylanases (WO 2006/078256), and *Thielavia terrestris* NRRL 8126 xylanases (WO 2009/079210). The xylanase may preferably be an endo-1,4-beta-xylanase, more preferably an endo-1,4-beta-xylanase of GH 10 or GH 11. Examples of commercial xylanases include Shearzyme® 500L, Bio-Feed™ Wheat (from Novozymes A/S), Econase® CE (from AB Enzymes GmbH), Depol™ 676 (from Biocatalysts Ltd.) and Multifect® Xylanase, Spezyme® CP (from Genencor Int.).

Examples of exo-1,4-beta-xylosidase useful in the methods of the present invention include, but are not limited to, *Trichoderma reesei* beta-xylosidase (UniProtKB/TrEMBL accession number Q92458), *Talaromyces emersonii* (SwissProt accession number Q8X212), and *Neurospora crassa* (SwissProt accession number Q7SOW4).

Examples of suitable bacterial xylanases include xylanases derived from a strain of *Bacillus*, such as *Bacillus subtilis*, such as the one disclosed in U.S. Pat. No. 5,306,633.

Xylanase may be added in an amount effective in the range from $0.16 \times 10^6$-$460 \times 10^6$ Units per ton beer mash or fermentation medium.

Mannanases as used herein are enzymes capable to break down the part of the hemicelluloses fraction consisting of mannans and heteromannans in plant walls. The mannanases as used in the present disclosure may be any mannanase either endo- and exo-β-1,4-mannanases but preferably exo-β-1,4-mannanse, in particular of microbial origin, in particular fungal or bacterial origin.

This may be a mannanase such as a mannanase derived from a strain of a filamentous fungus (e.g., *Aspergillus, Trichoderma, Phanerochaete*). Preferably, the mannanases act on different compositions of lignocellulosic material. Preferred mannanases for use in the present invention include endo-acting mannanases, exo-acting mannanases, and combinations thereof. Examples of commercially available mannanases suitable according to the present invention include, for example, Hemicell® (from Elanco Animal Health) and Purabrite® CP (from Genencor Int.).

Pectinase

The pectinase used in the present disclosure may be any pectinase, in particular of microbial origin, in particular of bacterial origin, such as a pectinase derived from a species within the genera *Bacillus, Clostridium, Pseudomonas, Xanthomonas* and *Erwinia*, or of fungal origin, such as a pectinase derived from a species within the genera *Trichoderma* or *Aspergillus*, in particular from a strain within the species *Aspergillus niger* and *Aspergillus aculeatus*. Contemplated commercially available pectinases include Pectinex® Ultra-SPL, Pectinex® Ultra Color (from Novozymes A/S), Rohapect® Classic, Rohapect® 10L (from AB Enzymes GmbH).

Pectinase may be added in an amount effective in the range from $1.4 \times 10^9$-$23500 \times 10^9$ Units per ton beer mash or fermentation medium.

Protease

The proteases as used in the present disclosure may be any protease, in particular of microbial origin, in particular of fungal and bacterial origin. Preferred proteases are acidic proteases, i.e., proteases characterized by the ability to hydrolyze proteins under acidic conditions below pH 7.

Suitable acid fungal proteases include fungal proteases derived from *Aspergillus, Mucor, Rhizopus, Candida, Coriolus, Endothia, Enthomophtra, Irpex, Penicillium, Sclerotium* and *Torlopsis*. Commercial proteases include GC 106™ and Spezyme® FAN (from Genencor Int.). Suitable microbial proteases, although not acidic proteases, include the commercially available products Alcalase® and Neutrase® (both from Novozymes A/S), EX-Protin (from C. Schliessmann Kellerei-Chemie GmbH & Co. KG) and Ronozyme® ProAct (from DSM Nutritional Products).

Cellulase

The cellulase as used in the present disclosure may be any cellulase, in particular of microbial origin, in particular fungal or bacterial origin such as a cellulase derived from a strain of a filamentous fungus (e.g., *Aspergillus, Trichoderma, Humicola, Fusarium*). Preferably, the cellulase acts on both cellulosic and lignocellulosic material. Preferred cellulases for use in the present invention include endo-acting cellulases, exo-acting celluases and cellobiases, and combinations thereof. Examples of commercially available cellulases suitable according to the present invention include, for example, Celluclast® (from Novozymes A/S), LAMINEX® and Spezyme® CP (from Genencor Int.) and Econase® CE (from AB Enzymes GmbH), Rohalase® BX (from AB Enzymes GmbH), Cellulase 13P (from Biocatalysts Ltd.).

Cellulase may be added in amounts effective in the range or from $0.03 \times 10^6$-$16 \times 10^6$ Units per ton beer or fermentation medium.

Glucanase

Glucan and chitin are far more resistant to microbial degradation than cellulose, which is the major constituent of the cell wall of many yeasts and fungi-like organisms. Glucan is predominantly beta-1,3-linked with some branching via 1,6-linkage (Manners et al., Biotechnol. Bioeng, 38, p. 977, 1973), and is known to be degradable by certain beta-1,3-glucanase systems. Beta-1,3-glucanase includes the group of endo-beta-1,3-glucanases also called laminarinases (E.C. 3.2.1.39 and E.C. 3.2.1.6, Enzyme Nomenclature, Academic Press, Inc. 1992). Beta-1,6-glucanases are enzymes hydrolyzing the beta-1,6-linkage in glucan.

The beta-1,3-glucanases as used in the present disclosure may be any 1,3-glucanase, in particular of microbial origin, in particular fungal or bacterial origin such as a beta-1,3-glucanase derivable from a strain of a filamentous fungus (e.g., *Aspergillus, Trichoderma, Penicillium, Humicola*). The beta-1,3-glucanases may preferably be an endo-1,3-beta-glucanase. The beta-1,6-glucanases as used in the present disclosure may be any 1,6-glucanase, in particular of microbial origin, in particular fungal or bacterial origin such as a beta-1,6-glucanase derivable from a strain of a filamentous fungus (e.g., *Aspergillus, Trichoderma, Penicillium, Humicola*). The beta-1,6-glucanases may preferably be an endo-1,6-beta-glucanase.

Examples for commercial available beta-1,3-glucanases suitable according to the present invention include, for example, Rohalase® BX (from AB Enzymes GmbH), Dyadic® Beta Glucanase BP CONC (from Dyadic International (USA), Inc.) and Rapidase® Glucalees (from DSM Food Specialties). Examples for commercial available beta-1,6-glucanases suitable according to the present invention include, for example, ThermoActive™ Pustulanase Ce1136 (from Prokazyme Ltd.).

1,3-glucanases and 1,6-glucanases may be added in an amount effective in the range from $0.08 \times 10^6$-$920 \times 10^6$ Units per ton beer mash or fermentation medium.

The inventions described and claimed herein are not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following example that should not be construed as limiting the scope of the invention.

Example

In the present example the increased production of xylose and arabinose during the fermentation process from starch-containing material using the fermenting microorganism wild-type yeast (*Saccharomyces cerevisiae*) in combination with the enzyme composition comprising xylanase and pectinase is described.

The efficiency of the fermentation process from starch-containing material to the product ethanol using a yeast cell suitable for fermentation of a sugar composition comprising C5 sugar(s) depends on the utilization of the C5 sugars in the substrate—this depends on the production and availability of the C5 during the fermentation process. Ethanol yield produced by pentose fermenting yeast cells will therefore depend on the availability, i.e., the titer of C5 sugars like xylose and arabinose. The higher the titer of xylose and arabinose the more ethanol can be produced by a pentose fermenting yeast cell.

Three different setups were tested. All setups were prepared in duplicates designated A and B.

In the first shake flasks (Setup #1 (shake flasks #1A/#1B)) the fermentation cultivation was not treated with enzymes (0 g/t xylanase; 0 g/t pectinase), in the second and third shake flasks (Setup #2 and #3) the fermentation cultivation was treated with the enzyme composition comprising a xylanase and a pectinase from the beginning of the fermentation. Two different concentrations were used:
Setup #2 (shake flasks #2A/#2B): 50 g/t xylanase and 50 g/t pectinase
Setup #3 (shake flaks #3A/#3B): 400 g/t xylanase and 400 g/t pectinase The tests were performed in 1 L shake flasks containing 400 mL fermentation culture. Fermentation locks were used on each shake flask. Samples were taken during the fermentation process and the concentrations of xylose and arabinose were determined by HPLC at the end of fermentation (63 h).

Examples

In one embodiment, the process of the production of ethanol from corn was performed as follows:
A) Process for Producing Fermentation Products
a) Reduction of the particle size of the starch-containing material by milling
  Corn (Pannonia, Hungary) was Milled to <2 mm particle size (coffee mill, BUNN)
b) Forming of a slurry comprising the starch-containing material and water
  Heating of 7.8 L warm tap water (water hardness 3.57 mmol/L) to 30° C. in a BIOSTAT® C fermentor (Sartorius AG)
  Addition of 8 mL α-amylase "α-amylase VF-Kartoffel" (C. Schliessmann Kellerei-Chemie GmbH & Co. KG, Nr. 5049)
  Addition of 4.2 kg milled corn to the heated tap water containing the α-amylase to obtain a 35% solid solution with a final volume of 12 L
c) Liquefying of the starch-containing material (Slurry)
  Increase of temperature to 90° C.
  Incubation of the fermentor for 90 min at 90° C. and 600 rpm
  Cooling of the slurry to 50° C.
d) Saccharifying of the liquefied material obtained
  Dilution of 6 mL glucoamylase "Amylase GA 500" (C. Schliessmann Kellerei-Chemie GmbH & Co. KG, Nr. 5042) in 25 mL tap water and subsequent addition to the 12 L slurry
  Dilution of 3.6 g (NH4)2SO4 (0.3 g/L) in 30 mL tap water and added to the 12 L slurry.
  Dilution of 36 g urea (3 g/L) in 60 mL tap water and addition to the 12 L slurry
  Stirring of the slurry containing 300 ppm ammonium sulphate and 3000 ppm urea in the BIOSTAT® C fermentor with 700 rpm for 2 hours for even distribution. Final product is designated as mash.
e) Fermentation
  Distribution of the mash into 1000 mL shake flasks in 400 g single portions
  Enzyme stock preparation: 2.5 g of the pectinase (Pec3) with 90349 U/mL and 2.5 g of the xylanase (Xyl16) with 10027 U/mL (see Table 1) were added into a 50 mL graduated cylinder and filled to 50 mL with tap water.

The enzyme stock was transferred into a 50 mL tube and then stored at 4° C. until use within one hour.

The following volumes of the enzyme stock preparation were added to the 1000 mL shake flasks containing 400 g of the mash. From each set up duplicates were made (designated A and B). Fermentation locks were used on each shake flask.

Shake flasks #1A and #1B: 0 mg of the enzyme stock preparation leading to 0 g/t of pectinase and 0 g/t of xylanase Shake flasks #2A and #2B: 200 mg of the enzyme preparation leading to 50 g/t of pectinase and 50 g/t of xylanase Shake flasks #3A and #3B: 1600 mg of the enzyme preparation leading to 400 g/t of pectinase and 400 g/t of xylanase Yeast propagation: 300 mL autoclaved YNB (yeast nitrogen base) medium plus glucose with 10 g/L glucose medium resulting in pH 5.7 in a 1 L cultivation flasks, which had been inoculated with 2 mL yeast (Ethanol RED®, Fermentis) from a −80° C. cryo stock containing 20% glycerol, were incubated for a minimum of 8 hours (30° C., 150 rpm) leading to the yeast culture.

Inoculation of each shake flask with 16 mL of the yeast culture.

Cultivations were carried out at 30° C. at 150 rpm for 63 hours. 7 mL samples were taken twice the day to monitor fermentation progress (ethanol concentration). The samples were transferred in 15 mL tubes and centrifuged at 4470 g for 10 min at 4° C. and stored until further analysis at −20° C.

B) Enzyme Product Activity Determination:

DNSA solution: For the DNSA solution the following compounds were used:

Dissolving 5.00 g 3,5-Dinitrosalicylic acid (DNSA) in 300 mL distilled $H_2O$

Addition of 50 mL NaOH/KOH-solution (4M KOH+4 M NaOH) drop by drop

Addition of 150 g K—Na-tartrate tetrahydrate

Cooling of solution to room temperature

Addition of distilled $H_2O$ to 500 mL final volume

Solution to be stored in the dark a) Pectinase

Substrates: Polygalacturonic acid (Sigma-Aldrich Co. LLC, 81325)

Substrates were dissolved in buffer to a concentration of 0.8% (w/v)

Buffer: 50 mM sodium acetate, pH 4.5

For the assay 96 well PCR microtiter plates (Greiner Bio-One Ltd.) were used. The enzymes were diluted in buffer. 90 µL substrate and 10 µL enzyme solution were mixed. A blank was measured replacing enzyme solution with water. Incubation was carried out for 30 min at 37° C., followed by a 5 min enzyme inactivation step at 99° C. and followed by cooling for 10 min at 4° C. In a second 96 well PCR microtiter plate (Greiner Bio-One Ltd.) 50 µL of the incubated substrate-enzyme mix was incubated with 50 µL of the DNSA solution at 98° C. for 10 min and then cooled to 4° C. and incubated for 5 min at 4° C.

100 µL of the reaction was transferred into a well of 96 well transparent, flat bottom microtiter plate and the adsorption was measured at 540 nm by a microtiter plate reader (Infinite® M1000 PRO, Tecan).

b) Xylanase

Substrates: Xylan from birchwood (Sigma-Aldrich Co. LLC, X0502)

Substrate was dissolved in buffer to a concentration of 1.5% (w/v)

Buffer: 100 mM sodium acetate, pH 5.0 containing 20 mM $CaCl_2$ and 0.4 g/L Tween20

For the assay 96 well PCR microtiter plate (Greiner Bio-One Ltd.) were used. The enzymes were diluted in buffer. 90 µL substrate and 10 µL enzyme solution were mixed. A blank was measured replacing enzyme solution with tap water. Incubation was carried out for 20 min at 40° C., followed by a 5 min enzyme inactivation step at 99° C. and followed by cooling for 5 min at 4° C. 45.5 µL of the DNSA solution was added to the 96 well PCR microtiter plate by a multidrop (Thermo Fisher Scientific Inc.), subsequently the plate was incubated at 98° C. for 10 min, then cooled to 4° C. and incubated for 5 min at 4° C.

100 µL of the reaction was transferred into a well of a new 96 well transparent, flat bottom micro titer plate and then the adsorption was measured at 540 nm by a micro titer plate reader (Infinite® M1000 PRO, Tecan).

The activity is calculated as Units per µL or mg of enzyme product. 1 Unit is defined as the amount of formed reducing ends in µmol per minute. The enzyme activities are shown in Table 1.

TABLE 1

| Type | Activity | Shortname |
|---|---|---|
| pectinase | 90349 U/mL | Pec3 |
| xylanase | 10027 U/mL | Xyl16 |

Analysis of Xylose and Arabinose

Frozen samples of the fermentation process were thawed and the xylose and the arabinose concentrations in the fermentation samples were measured by HPLC. Fermentation samples were centrifuged at 20000 g at 10° C. for 15 min and the supernatant was transferred into HPLC vials. The samples (30 µL) were injected into a VWR/Hitachi equipment comprising the isocratic pump L-2130, the autosampler L-2200, the column oven L-2350, the refractic index detector L-2490 and a degasser at 10° C. The EZ Chrome Elite 3.3.1 software was used. The VWR/Hitachi HPLC was equipped with a Rezex ROA Organic Acid H+(8%) LC column (300×7.8 mm, Phenomenex Inc.) and a guard column (carbo-H 4×3.0 mm, PhenomenexInc.). The column was eluted with 0.0025 M $H_2SO_4$ at 0.45 mL/min flow rate at 60° C. The system was standardized by a 5-point calibration xylose or arabinose standard (10 g/L, 5 g/L, 2 g/L, 1 g/L, 0.5 g/L and 0 g/L xylose or arabinose).

TABLE 2

| | xylose [g/L] | | | | | |
|---|---|---|---|---|---|---|
| | 0 g/t pectinase plus | | 50 g/t pectinase plus 50 g/t xylanase | | 400 g/t pectinase plus 400 g/t xylanase | |
| | 0 g/t xylanase | | Average of | | Average of | |
| Growth time [h] | Average of parallel set ups | Deviation from Average | parallel set ups | Deviation from Average | parallel set ups | Deviation from Average |
| 63 | 0.20 | 0.001 | 0.26 | 0.001 | 0.55 | 0.014 |

TABLE 3

| | arabinose [g/L] | | | | | |
|---|---|---|---|---|---|---|
| | 0 g/t pectinase plus | | 50 g/t pectinase plus 50 g/t xylanase | | 400 g/t pectinase plus 400 g/t xylanase | |
| | 0 g/t xylanase | | Average of | | Average of | |
| Growth time [h] | Average of parallel set ups | Deviation from Average | parallel set ups | Deviation from Average | parallel set ups | Deviation from Average |
| 63 | 0.25 | 0.000 | 0.43 | 0.002 | 0.98 | 0.017 |

Table 2 and Table 3 show that treatment with the enzyme composition comprising a xylanase and a pectinase (50 g/t and 400 g/t of both enzymes) increases the titer of the C5 sugars xylose and arabinose compared to the absence of the enzyme composition (0 g/t of pectinase plus xylanase).

Therefore, the enzyme composition comprising a xylanase and a pectinase increases the availability of the substrate, i.e., pentose substrates xylose and arabinose, which can be converted to ethanol by pentose fermenting yeast cells. Thus, as a result of the addition of the enzyme composition comprising a xylanase and a pectinase the ethanol yield produced by pentose fermenting yeast cells is increased.

What is claimed is:

1. A method of producing a fermentation product from starch-containing material comprising:
   i) Converting starch-containing material to fermentable sugars;
   ii) Subjecting the fermentable sugars to an enzyme composition comprising a hemicellulase and at least a further enzyme selected from the group consisting of pectinase, cellulase, glucanase and protease;
   iii) Fermenting the fermentable sugars with fermenting microorganisms to beer mash; and
   iv) Separating the fermentation product in the beer mash, wherein the fermenting microorganisms comprise pentose fermenting yeast cells and/or pentose and glucose fermenting yeast cells.

2. The method according to claim 1, wherein the fermenting microorganisms comprise a glucose fermenting microorganism, selected from the group consisting of fungi, yeast and/or and bacteria.

3. The method according to claim 1, wherein the fermenting microorganisms comprise *Saccharomyces cerevisiae* or baker's yeast.

4. The method according to claim 1, wherein the enzyme composition comprises a combination selected from the group consisting of:
   i) a hemicellulase, cellulase and a glucanase;
   ii) a hemicellulase, pectinase and a glucanase;
   iii) a hemicellulase and a pectinase;
   iv) a hemicellulase and a glucanase; and
   v) a hemicellulase and a cellulose.

5. The method according to claim 1, wherein the fermentation product is selected from the group consisting of an acid, an alcohol and hydrogen.

6. The method according to claim 5, wherein the alcohol is selected from the group consisting of ethanol, butanol, propanol, methanol, propanediol and butanediol.

7. The method according to claim 5, wherein the acid is selected from the group consisting of lactic acid, propionic acid, acetic acid, succinic acid, malic acid, butyric acid and formic acid.

8. The method according to claim 1, wherein the starch-containing material is obtained from cereals and/or tubers.

9. The method according to claim 1, wherein the starch-containing material is selected from the groups consisting of corn, wheat, barley, rye, millet, sorghum, and milo.

* * * * *